US012623019B2

(12) United States Patent
Breton et al.

(10) Patent No.: US 12,623,019 B2
(45) Date of Patent: May 12, 2026

(54) SYSTEM, METHOD, AND COMPUTER READABLE MEDIUM FOR DYNAMIC INSULIN SENSITIVITY IN DIABETIC PUMP USERS

(71) Applicant: UNIVERSITY OF VIRGINIA PATENT FOUNDATION, Charlottesville, VA (US)

(72) Inventors: Marc D. Breton, Charlottesville, VA (US); Boyi Jiang, Charlottesville, VA (US); Chiara Fabris, Charlottesville, VA (US)

(73) Assignee: UNIVERSITY OF VIRGINIA PATENT FOUNDATION, Charlottesville, VA (US)

( * ) Notice: Subject to any disclaimer, the term of this patent is extended or adjusted under 35 U.S.C. 154(b) by 1148 days.

(21) Appl. No.: 16/583,456

(22) Filed: Sep. 26, 2019

(65) Prior Publication Data

US 2020/0023126 A1 Jan. 23, 2020

Related U.S. Application Data

(63) Continuation of application No. 15/255,828, filed on Sep. 2, 2016, now Pat. No. 10,463,789.

(Continued)

(51) Int. Cl.
*A61M 5/172* (2006.01)
*A61B 5/00* (2006.01)
(Continued)

(52) U.S. Cl.
CPC ......... *A61M 5/1723* (2013.01); *A61B 5/1451* (2013.01); *A61B 5/14532* (2013.01);
(Continued)

(58) Field of Classification Search
CPC ...... A61M 5/1723; A61M 2005/14208; A61M 2230/201; A61B 5/1451; A61B 5/14532;
(Continued)

(56) References Cited

U.S. PATENT DOCUMENTS 6,923,763 B1 8/2005 Kovatchev et al.
7,025,425 B2 4/2006 Kovatchev et al.
(Continued)

FOREIGN PATENT DOCUMENTS

WO 0113786 A1 3/2001
WO 0172208 A2 10/2001
(Continued)

OTHER PUBLICATIONS

Herrero et al, A Simple Robust Method for Estimating the Glucose Rate of Appearance from Mixed Meals, Journal of Diabetes Science and Technology, vol. 6, Issue 1, Jan. 2012, pp. 153-162 (Year: 2012).*

(Continued)

*Primary Examiner* — Puya Agahi
(74) *Attorney, Agent, or Firm* — Buchanan Ingersoll & Rooney PC

(57) ABSTRACT

A technique for treating diabetes that recognizes patient insulin sensitivity is a time-varying physiological parameter. The described techniques for treating diabetes include measuring interstitial fluid glucose concentration, reading insulin delivery data, determining patient insulin sensitivity based on the interstitial fluid glucose concentration and insulin delivery data, and a time-varying physiological parameter, and dispensing an insulin dose from an insulin delivery device based on the determined patient insulin sensitivity.

18 Claims, 6 Drawing Sheets

Related U.S. Application Data

(60) Provisional application No. 62/213,198, filed on Sep. 2, 2015.

(51) Int. Cl.

| | |
|---|---|
| *A61B 5/145* | (2006.01) |
| *A61M 5/142* | (2006.01) |
| *G16H 20/10* | (2018.01) |
| *G16H 20/13* | (2018.01) |
| *G16H 20/17* | (2018.01) |
| *G16H 40/60* | (2018.01) |
| *G16H 40/63* | (2018.01) |
| *G16H 50/20* | (2018.01) |

(52) U.S. Cl.
CPC .......... *A61B 5/4839* (2013.01); *A61B 5/7275* (2013.01); *G16H 20/10* (2018.01); *G16H 20/13* (2018.01); *G16H 20/17* (2018.01); *G16H 40/60* (2018.01); *G16H 40/63* (2018.01); *G16H 50/20* (2018.01); *A61M 2005/14208* (2013.01); *A61M 2230/201* (2013.01)

(58) Field of Classification Search
CPC .... A61B 5/4839; A61B 5/7275; G16H 20/10; G16H 20/13; G16H 20/17; G16H 40/60; G16H 40/63; G16H 50/20
See application file for complete search history.

(56) References Cited

U.S. PATENT DOCUMENTS

| | | | |
|---|---|---|---|
| 7,815,569 B2 | 10/2010 | Kovatchev et al. | |
| 7,874,985 B2 | 1/2011 | Kovatchev et al. | |
| 8,135,548 B2 | 3/2012 | Breton et al. | |
| 8,538,703 B2 | 9/2013 | Kovatchev et al. | |
| 8,562,587 B2 | 10/2013 | Kovatchev et al. | |
| 8,585,593 B2 | 11/2013 | Kovatchev et al. | |
| 8,718,958 B2 | 5/2014 | Breton et al. | |
| 2004/0094733 A1* | 5/2004 | Hower | A61B 5/14514 |
| | | | 251/11 |
| 2004/0254433 A1* | 12/2004 | Bandis | A61B 5/6849 |
| | | | 600/347 |
| 2004/0260162 A1* | 12/2004 | Rohleder | G01N 21/65 |
| | | | 600/316 |
| 2005/0183954 A1* | 8/2005 | Hitchcock | A61B 5/6852 |
| | | | 600/300 |
| 2008/0154513 A1 | 6/2008 | Kovatchev et al. | |
| 2008/0183060 A1* | 7/2008 | Steil | C12Y 301/01003 |
| | | | 606/151 |
| 2008/0314385 A1 | 12/2008 | Brunner et al. | |
| 2008/0314395 A1 | 12/2008 | Kovatchev et al. | |
| 2009/0171589 A1 | 7/2009 | Kovatchev | |
| 2010/0125241 A1* | 5/2010 | Prud'homme | G16H 20/17 |
| | | | 600/300 |
| 2010/0179768 A1 | 7/2010 | Kovatchev et al. | |
| 2010/0198520 A1 | 8/2010 | Breton et al. | |
| 2010/0249561 A1 | 9/2010 | Patek et al. | |
| 2011/0077930 A1* | 3/2011 | Alferness | G16Z 99/00 |
| | | | 703/11 |
| 2011/0098548 A1 | 4/2011 | Budiman et al. | |
| 2011/0264374 A1 | 10/2011 | Johnson et al. | |
| 2011/0264378 A1 | 10/2011 | Breton et al. | |
| 2012/0004512 A1 | 1/2012 | Kovatchev et al. | |
| 2012/0078067 A1 | 3/2012 | Kovatchev et al. | |
| 2012/0130698 A1 | 5/2012 | Kovatchev et al. | |
| 2012/0191361 A1 | 7/2012 | Kovatchev et al. | |
| 2012/0245556 A1 | 9/2012 | Kovatchev et al. | |
| 2013/0079613 A1 | 3/2013 | Kovatchev et al. | |
| 2013/0116649 A1 | 5/2013 | Breton et al. | |
| 2013/0137953 A1* | 5/2013 | Harper | A61B 5/14503 |
| | | | 600/365 |
| 2013/0217979 A1* | 8/2013 | Blackadar | A61B 5/1123 |
| | | | 600/301 |
| 2014/0046159 A1 | 2/2014 | Kovatchev et al. | |
| 2014/0066892 A1* | 3/2014 | Keenan | A61B 5/14532 |
| | | | 604/506 |
| 2014/0215239 A1 | 7/2014 | Kovatchev et al. | |
| 2014/0244216 A1 | 8/2014 | Breton et al. | |
| 2015/0018633 A1 | 1/2015 | Kovachev et al. | |
| 2015/0190098 A1 | 7/2015 | Patek et al. | |
| 2015/0193589 A1 | 7/2015 | Ortiz et al. | |
| 2016/0354543 A1 | 12/2016 | Cinar et al. | |

FOREIGN PATENT DOCUMENTS

| | | | |
|---|---|---|---|
| WO | 02067776 A1 | 9/2002 | |
| WO | 2005106017 A2 | 11/2005 | |
| WO | 2007027691 A1 | 3/2007 | |
| WO | 2007081853 A2 | 7/2007 | |
| WO | 2008052199 A2 | 5/2008 | |
| WO | 2008067284 A2 | 6/2008 | |
| WO | 2008157781 A1 | 12/2008 | |
| WO | WO-2009009528 A2 * | 1/2009 | ............ G06F 19/00 |
| WO | 2010062898 A1 | 6/2010 | |
| WO | 2010099313 A1 | 9/2010 | |
| WO | 2010138848 A1 | 12/2010 | |
| WO | 2010151834 A1 | 12/2010 | |
| WO | 2011028731 A1 | 3/2011 | |
| WO | 2011028925 A1 | 3/2011 | |
| WO | 2011112974 A1 | 9/2011 | |
| WO | 2011119832 A1 | 9/2011 | |
| WO | 2012178113 A1 | 12/2012 | |
| WO | 2012178134 A2 | 12/2012 | |
| WO | 2013032965 A1 | 3/2013 | |
| WO | 2013177565 A1 | 11/2013 | |
| WO | 2014022864 A1 | 2/2014 | |
| WO | 2014130841 A1 | 8/2014 | |
| WO | 2015003124 A2 | 1/2015 | |
| WO | 2015103543 A1 | 7/2015 | |

OTHER PUBLICATIONS

"Continuous Glucose Monitoring and Intensive Treatment of Type 1 Diabetes," N. Engl. J. Med., vol. 359, No. 14, Oct. 2008, pp. 1464-1476.

A.Caumo, A., et al., "Insulin Sensitivity from Meal Tolerance Tests in Normal Subjects: A Minimal Model Index," J. Clin.endocrinol. Metab. vol. 85, No. 11, pp. 419-429.

Basu, A., et al., "Time Lag of Glucose From Intravascular to Interstitial Compartment in Type 1 Diabetes," J. Diabetes Sci. Technol. vol. 9, No. 1, pp. 63-68.

Bergman, R. N., et al. , "Quantitative estimation of insulin sensitivity", Am. J. Physiol.-Endocrinol. Metab., vol. 236,—No. 6, p. E667.

Boden, G., et al., "Evidence for a Circadian Rhythm of Insulin Sensitivity in Patients With NIDDM Caused by Cyclic Changes in Heptic Glucose Production", Diabetes, vol. 45, No. 8, pp. 1044-1050.

Borgouhts, L. B. , et al., "Exercise and insulin sensitivity: a review", Int. J. Sports Med., vol. 21, No. 1, pp. 1-12.

Breton, M. , et al., "Analysis, Modeling, and Simulation of the Accuracy of Continuous Glucose Sensors,", J. Diabetes Sci. Technol., vol. 2, No. 5, pp. 853-862,.

Christiansen, M., et al., "A New-Generation Continuous Glucose Monitoring System: Improved Accuracy and Reliability Compared with a Previous-Generation System", Diabetes Technol. Ther., vol. 15, No. 10, pp. 881-888.

Clarke, W. L , et al., "Closed-loop artificial pancreas using subcutaneous glucose sensing and insulin delivery and a model predictive control algorithm: the Virginia experience", J. Diabetes Sci. Technol., vol. 3, No. 5 , pp. 1031-1038.

Defronzo, R. A., et al., "Glucose clamp technique: a method for quantifying insulin secretion and resistance", Am J.Physiol, vol. 237, No. 3, pp. E214-E223.

Goodyear, L. J., et al., "Exercise, Glucose Transport, and Insulin Sensitivity", Annu. Rev. Med., vol. 49, No. 1, pp. 235-261.

(56)                    References Cited

OTHER PUBLICATIONS

Grosman, B., et al., "Zone model predictive control: a strategy to minimize hyper- and hypoglycemic events", J.Diabetes Sci Technol, vol. 4, No. 4, pp. 961-975.

Kamath, A., et al., "Analysis of Time Lags and Other Sources of Error of the DexCom SEVEN Continuous Glucose Monitor", Diabetes Technol. Ther., vol. 11, No. 11, pp. 689-695.

Kovatchev, B. P., et al., "Symmetrization of the Blood Glucose Measurement Scale and Its Applications", Diabetes, vol. 20, No. 11, pp. 1655-1658.

Kovatchev, B. P., et al., "In silico preclinical trials: a proof of concept in closed-loop control of type 1 diabetes", J.Diabetes Sci. Technol, vol. 3, No. 1, pp. 44-55.

Lin, J., et al., "Stochastic modelling of insulin sensitivity and adaptive glycemic control for critical care", Comput.Methods Programs Biomed., vol. 89, No. 2, pp. 141-152.

Man, et al., "Insulin sensitivity by oral glucose minimal models: validation against clamp", Am. J. Physiol. Endocnnol. Metab., vol. 289, No. 6, Dec. 2005, pp. E954-E959.

Man, C.D., et al., "A System Model of Oral Glucose Absorption: Validation on Gold Standard Data", IEEE Trans.Biomed. Eng, vol. 53, No. 12, pp. 2472-2478.

Man, C.D., et al., "Minimal model estimation of glucose absorption and insulin sensitivity from oral test: validation with a" , Am. J_ Physiol.-Endocrinol. Metab., vol. 287, No. 4, pp. E954-E959.

Man, C.D. , et al. , "The oral glucose minimal model: Estimation of insulin sensitivity from a meal test", IEEE Trans. biomed. Eng_, vol. 49, No. 5 , pp. 419-429.

Mcmahon, S. K. , et al. , "Glucose Requirements to Maintain Euglycemia after Moderate-Intensity Afternoon Exercise in Adolescents with Type 1 Diabetes Are Increased in a Biphasic Manner", J. Clin. Endocrinol. Metab., vol. 92, No. 3, , pp. 963-968.

Pilloneto, G. , et al. , "Dynamic insulin sensitivity index: importance in diabetes", Am. J. Physiol.-Endocrinol. Metab vol. 298, No. 3 , pp. E440-E448.

Riccardi, G. , et al. , "Dietary fat, insulin sensitivity and the metabolic syndrome,", Clin. Nutr. Edinb. Scotl., vol. 23, No. 4 , pp. 447-456.

Schiavon, M. , et al. , "Quantitative Estimation of Insulin Sensitivity in Type 1 Diabetic Subjects Wearing a Sensor Augmented", Diabetes Care, vol. 37, No. 5 , pp. 1216-1223.

Steil, G. M. , et al. , "Determination of Plasma Glucose During Rapid Glucose Excursions with a Subcutaneous Glucose Sensor", Diabetes Technol. Ther., vol. 5, No. 1 , pp. 27-31.

Volskanyan, G. , et al. , "Putative Delays in Interstitial Fluid (ISF) Glucose Kinetics Can Be Attributed to the Glucose Sensing Systems Used to Measure Them Rather than the Delay in ISF Glucose Itself", J. Diabetes Sci. Technol., vol. 1, No. 5, , pp. 639-644.

* cited by examiner

<u>200</u>

300

600

SYSTEM, METHOD, AND COMPUTER READABLE MEDIUM FOR DYNAMIC INSULIN SENSITIVITY IN DIABETIC PUMP USERS

RELATED APPLICATIONS

This application is a continuation of U.S. patent application Ser. No. 15/255,828 filed Sep. 2, 2016, which claims the benefit under 35 U.S.C. § 119 of U.S. Provisional Patent Application No. 62/213,198 filed on Sep. 2, 2015, the entire contents of which are hereby incorporated by reference in their entireties.

FIELD

The present disclosure provides system, method, and computer readable medium for dispensing insulin to a patient that recognizes patient insulin sensitivity varies over time.

BACKGROUND

Insulin is a hormone needed by the body to absorb glucose from the blood into fat, liver, and skeletal muscle cells, among others. Patients with diabetes either do not produce insulin (type 1 diabetes) or produce insulin but are resistant to insulin's effects (type 2 diabetes) and so their bodies cannot break down the sugars and starches from food into glucose for use as energy by the body. Patients with type 1 and type 2 diabetes can treat their condition in multiple ways including dietary changes, exercise, non-insulin based medications, or insulin. The non-insulin medication may come in the form of an oral agent, for example, and the insulin may be delivered in multiple ways including syringes, pre-filled insulin pens, or an insulin pump. Some patients may be prescribed treatment regimes that employ several treatments for their complementary effects. For example, a patient may receive a non-insulin based medication in addition to insulin when the non-insulin based medication is designed to improve the patient's responsiveness to insulin. Examples of non-insulin medications include forms of biguanides, sulfonylureas, megalitindes, d-phenylalanine derivatives, thiazolidinediones, pioglitazones, DDP-4 inhibitors, alpha-glucosidase inhibitors, and bile acid sequestrants. Another patient may instead receive a different combination of rapid-acting, short-acting, intermediate-acting, long-acting, and pre-mixed insulin, depending on the patient's symptoms, and based on the patient's insulin sensitivity. Examples of possible delivery methods of these different types of insulin include syringes, insulin pens, insulin pumps, jet injectors, inhaled insulin, and the like. Based on the understanding of a patient's physiology, different combinations of these different treatments are prescribed by medical professionals to manage a patient's diabetes.

Insulin sensitivity (SI) is an index that describes the effectiveness of a patient's insulin reaction to glucose. In the late 1970s, a hyperinsulinemic-euglycemic clamp technique was proposed for measuring the whole-body SI in the hospital setting. Two alternatives to the hyperinsulinemic-euglycemic clamp technique were intravenous glucose tolerance tests (VGTT) and oral glucose tolerance tests (OGTT). In VGTT and OGTT, a predetermined amount of glucose is intravenously or orally dosed and the results measured. An oral minimal model is a useful tool for insulin sensitivity estimation based on OGTT data. Although these traditional techniques are effective and robust, the patient must be in an inpatient clinical setting either with intravenous lines attached or the patient must endure multiple venipunctures. These procedures are invasive to the patient, disrupt the patients' daily insulin treatment in the home or other setting, and only provide a one data point as to the patient's condition. Accordingly, the above described treatment regimes for diabetic patients did not consider the possibility that a patient's insulin sensitivity could vary over time.

Recently, improvements in medical technology have allowed for more comprehensive glucose monitoring of the patient through the use of wearable glucose monitors, for example. In addition, insulin pumps have been miniaturized so that patients can easily adjust the insulin dose as needed, and insulin pens have begun including wireless technologies to report various types of information. The advent of these glucose monitors and insulin delivery systems have improved patients' ability to understand their condition and to conveniently manage their own treatment, within the boundaries set by their medical professionals.

Although others, including those mentioned below in the Background References section, have proposed estimating a patient's insulin sensitivity using pump data and continuous glucose monitoring data, those who have previously estimated insulin sensitivity assumed that insulin sensitivity was a time invariant physiological parameter at least during the testing process. Studies have, however, shown that insulin sensitivity does vary significant in response to a variety of factors including circadian rhythm, physical activity, dietary habits, and illness or stress. Dynamic insulin sensitivity indexes were therefore devised to address this improved understanding, and it has been demonstrated that stochastic modeling can provide first order estimates of insulin sensitivity. The application of the improved understanding of the dynamic nature of a patient's insulin sensitivity has not, however, been incorporated into a patient's treatment regime.

The techniques described here consider insulin sensitivity to be a time-varying physiological parameter and utilizes continuous glucose monitoring and insulin delivery data to quantify insulin sensitivity of the patient over time. Further, insulin sensitivity can be used for tracking the state of the patient's condition and adjust the treatment plans so that the appropriate treatment regime is applied to a patient.

BACKGROUND REFERENCES

The following background references are hereby incorporated by reference in their entirety herein:

R. A. DeFronzo, J. D. Tobin, and R. Andres, "Glucose clamp technique: a method for quantifying insulin secretion and resistance," Am. J. Physiol., vol. 237, no. 3, pp. E214-223, September 1979.

R. N. Bergman, Y. Z. Ider, C. R. Bowden, and C. Cobelli, "Quantitative estimation of insulin sensitivity.," Am. J. Physiol.-Endocrinol. Metab., vol. 236, no. 6, p. E667, June 1979.

A. Caumo, R. N. Bergman, and C. Cobelli, "Insulin Sensitivity from Meal Tolerance Tests in Normal Subjects: A Minimal Model Index," J. Clin. Endocrinol. Metab., vol. 85, no. 11, pp. 4396-4402, November 2000.

C. D. Man, A. Caumo, and C. Cobelli, "The oral glucose minimal model: Estimation of insulin sensitivity from a meal test," IEEE Trans. Biomed. Eng., vol. 49, no. 5, pp. 419-429, May 2002.

C. D. Man, A. Caumo, R. Basu, R. Rizza, G. Toffolo, and C. Cobelli, "Minimal model estimation of glucose absorption and insulin sensitivity from oral test: validation with a tracer method," Am. J. Physiol.-Endocrinol. Metab., vol. 287, no. 4, pp. E637-E643, October 2004.

C. D. Man, K. E. Yarasheski, A. Caumo, H. Robertson, G. Toffolo, K. S. Polonsky, and C. Cobelli, "Insulin sensitivity by oral glucose minimal models: validation against clamp," Am. J. Physiol.-Endocrinol. Metab., vol. 289, no. 6, pp. E954-E959, December 2005.

M. Schiavon, C. D. Man, Y. C. Kudva, A. Basu, and C. Cobelli, "Quantitative Estimation of Insulin Sensitivity in Type 1 Diabetic Subjects Wearing a Sensor-Augmented Insulin Pump," Diabetes Care, vol. 37, no. 5, pp. 1216-1223, May 2014.

G. Boden, X. Chen, and J. L. Urbain, "Evidence for a Circadian Rhythm of Insulin Sensitivity in Patients With NIDDM Caused by Cyclic Changes in Hepatic Glucose Production," Diabetes, vol. 45, no. 8, pp. 1044-1050, August 1996.

L. B. Borghouts and H. A. Keizer, "Exercise and insulin sensitivity: a review," Int. J. Sports Med., vol. 21, no. 1, pp. 1-12, January 2000.

G. Riccardi, R. Giacco, and A. A. Rivellese, "Dietary fat, insulin sensitivity and the metabolic syndrome," Clin. Nutr. Edinb. Scotl., vol. 23, no. 4, pp. 447-456, August 2004.

G. Pillonetto, A. Caumo, and C. Cobelli, "Dynamic insulin sensitivity index: importance in diabetes," Am. J. Physiol.-Endocrinol. Metab., vol. 298, no. 3, pp. E440-E448, March 2010.

J. Lin, D. Lee, J. G. Chase, G. M. Shaw, A. Le Compte, T. Lotz, J. Wong, T. Lonergan, and C. E. Hann, "Stochastic modelling of insulin sensitivity and adaptive glycemic control for critical care," Comput. Methods Programs Biomed., vol. 89, no. 2, pp. 141-152, February 2008.

C. D. Man, M. Camilleri, and C. Cobelli, "A System Model of Oral Glucose Absorption: Validation on Gold Standard Data," IEEE Trans. Biomed. Eng., vol. 53, no. 12, pp. 2472-2478, December 2006.

B. Grosman, E. Dassau, H. C. Zisser, L. Jovanovic, and F. J. Doyle 3rd, "Zone model predictive control: a strategy to minimize hyper- and hypoglycemic events," J. Diabetes Sci. Technol., vol. 4, no. 4, pp. 961-975, July 2010.

R. F. Stengel, Optimal Control and Estimation. Courier Corporation, 2012.

"Continuous Glucose Monitoring and Intensive Treatment of Type 1 Diabetes," N. Engl. J. Med., vol. 359, no. 14, pp. 1464-1476, October 2008.

B. P. Kovatchev, M. Breton, C. D. Man, and C. Cobelli, "In silico preclinical trials: a proof of concept in closed-loop control of type 1 diabetes," J. Diabetes Sci. Technol., vol. 3, no. 1, pp. 44-55, January 2009.

W. L. Clarke, S. Anderson, M. Breton, S. Patek, L. Kashmer, and B. Kovatchev, "Closed-loop artificial pancreas using subcutaneous glucose sensing and insulin delivery and a model predictive control algorithm: the Virginia experience," J. Diabetes Sci. Technol., vol. 3, no. 5, pp. 1031-1038, September 2009.

G. Voskanyan, D. B. Keenan, J. J. Mastrototaro, and G. M. Steil, "Putative Delays in Interstitial Fluid (ISF) Glucose Kinetics Can Be Attributed to the Glucose Sensing Systems Used to Measure Them Rather than the Delay in ISF Glucose Itself," J. Diabetes Sci. Technol., vol. 1, no. 5, pp. 639-644, September 2007.

A. Kamath, A. Mahalingam, and J. Brauker, "Analysis of Time Lags and Other Sources of Error of the DexCom SEVEN Continuous Glucose Monitor," Diabetes Technol. Ther., vol. 11, no. 11, pp. 689-695, November 2009.

G. M. Steil, K. Rebrin, J. Mastrototaro, B. Bernaba, and M. F. Saad, "Determination of Plasma Glucose During Rapid Glucose Excursions with a Subcutaneous Glucose Sensor," Diabetes Technol. Ther., vol. 5, no. 1, pp. 27-31, February 2003.

A. Basu, S. Dube, S. Veettil, M. Slama, Y. C. Kudva, T. Peyser, R. E. Carter, C. Cobelli, and R. Basu, "Time Lag of Glucose From Intravascular to Interstitial Compartment in Type 1 Diabetes," J. Diabetes Sci. Technol., vol. 9, no. 1, pp. 63-68, January 2015.

M. Breton and B. Kovatchev, "Analysis, Modeling, and Simulation of the Accuracy of Continuous Glucose Sensors," J. Diabetes Sci. Technol., vol. 2, no. 5, pp. 853-862, September 2008.

M. Christiansen, T. Bailey, E. Watkins, D. Liljenquist, D. Price, K. Nakamura, R. Boock, and T. Peyser, "A New-Generation Continuous Glucose Monitoring System: Improved Accuracy and Reliability Compared with a Previous-Generation System," Diabetes Technol. Ther., vol. 15, no. 10, pp. 881-888, June 2013.

B. P. Kovatchev, D. J. Cox, L. A. Gonder-Frederick, and W. Clarke, "Symmetrization of the Blood Glucose Measurement Scale and Its Applications," Diabetes Care, vol. 20, no. 11, pp. 1655-1658, November 1997.

L. J. Goodyear PhD and B. B. Kahn MD, "Exercise, Glucose Transport, and Insulin Sensitivity," Annu. Rev. Med., vol. 49, no. 1, pp. 235-261, 1998.

S. K. McMahon, L. D. Ferreira, N. Ratnam, R. J. Davey, L. M. Youngs, E. A. Davis, P. A. Fournier, and T. W. Jones, "Glucose Requirements to Maintain Euglycemia after Moderate-Intensity Afternoon Exercise in Adolescents with Type 1 Diabetes Are Increased in a Biphasic Manner," J. Clin. Endocrinol. Metab., vol. 92, no. 3, pp. 963-968, March 2007.

U.S. patent application Ser. No. 14/419,375 entitled "Computer Simulation for Testing and Monitoring of Treatment Strategies for Stress Hyperglycemia", filed Feb. 3, 2015.

International Patent Application No. PCT/US2013/053664 entitled "Computer Simulation for Testing and Monitoring of Treatment Strategies for Stress Hyperglycemia", filed Aug. 5, 2013; International Patent Application Publication No. WO 2014/022864, Feb. 6, 2014.

International Patent Application No. PCT/US2015/010167 entitled "Central Data Exchange Node For System Monitoring and Control of Blood Glucose Levels in Diabetic Patients", filed Jan. 5, 2015.

International Patent Application No. PCT/US2014/045393 entitled "Simulation of Endogenous and Exogenous Glucose/Insulin/Glucagon Interplay in Type 1 Diabetic Patients", filed Jul. 3, 2014; International Patent Application Publication No. WO 2015/003124, Jan. 8, 2015.

U.S. patent application Ser. No. 14/266,612 entitled "Method, System and Computer Program Product for Real-Time Detection of Sensitivity Decline in Analyte Sensors", filed Apr. 30, 2014; U.S. Patent Application Publication No. 2014/0244216, Aug. 28, 2014.

U.S. patent application Ser. No. 13/418,305 entitled "Method, System and Computer Program Product for Real-Time Detection of Sensitivity Decline in Analyte Sensors", filed Mar. 12, 2012; U.S. Pat. No. 8,718,958, issued May 6, 2014.

International Patent Application No. PCT/US2007/082744 entitled "Method, System and Computer Program Product for Real-Time Detection of Sensitivity Decline in Analyte Sensors", filed Oct. 26, 2007; International Patent Application Publication No. WO/2008/052199, May 2, 2008.

U.S. patent application Ser. No. 11/925,689 entitled "Method, System and Computer Program Product for Real-Time Detection of Sensitivity Decline in Analyte Sensors", filed Oct. 26, 2007; U.S. Pat. No. 8,135,548, issued Mar. 13, 2012.

U.S. patent application Ser. No. 14/241,383 entitled "Method, System and Computer Readable Medium for Adaptive Advisory Control of Diabetes", filed Feb. 26, 2014.

International Patent Application No. PCT/US2012/052422 entitled "Method, System and Computer Readable Medium for Adaptive Advisory Control of Diabetes", filed Aug. 26, 2012; International Patent Application Publication No. WO 2013/032965, Mar. 7, 2013.

International Patent Application No. PCT/US2014/017754 entitled "Method and System for Model-Based Tracking of Changes in Average Glycemia in Diabetes", filed Feb. 21, 2014; International Patent Application Publication No. WO 2014/130841, Aug. 28, 2014.

U.S. patent application Ser. No. 14/128,922 entitled "Unified Platform For Monitoring and Control of Blood Glucose Levels in Diabetic Patients", filed Dec. 23, 2013; U.S. Patent Application Publication No. 2015/0018633, Jan. 15, 2015.

International Patent Application No. PCT/US2012/043910 entitled "Unified Platform For Monitoring and Control of Blood Glucose Levels in Diabetic Patients", filed Jun. 23, 2012; International Patent Application Publication No. WO 2012/178134, Dec. 27, 2012.

U.S. patent application Ser. No. 14/128,811 entitled "Methods and Apparatus for Modular Power Management and Protection of Critical Services in Ambulatory Medical Devices", filed Dec. 23, 2013; U.S. Patent Application Publication No. 2014/0215239, Jul. 31, 2014.

International Patent Application No. PCT/US2012/043883 entitled "Methods and Apparatus for Modular Power Management and Protection of Critical Services in Ambulatory Medical Devices", filed Jun. 22, 2012; International Patent Application Publication No. WO 2012/178113, Dec. 27, 2012.

U.S. patent application Ser. No. 14/015,831 entitled "CGM-Based Prevention of Hypoglycemia Via Hypoglycemia Risk Assessment and Smooth Reduction Insulin Delivery", filed Aug. 30, 2013; U.S. Patent Application Publication No. 2014/0046159, Feb. 13, 2014.

U.S. patent application Ser. No. 13/203,469 entitled "CGM-Based Prevention of Hypoglycemia via Hypoglycemia Risk Assessment and Smooth Reduction Insulin Delivery", filed Aug. 25, 2011; U.S. Pat. No. 8,562,587, issued Oct. 22, 2013.

International Patent Application No. PCT/US2010/025405 entitled "CGM-Based Prevention of Hypoglycemia via Hypoglycemia Risk Assessment and Smooth Reduction Insulin Delivery", filed Feb. 25, 2010; International Patent Application Publication No. WO 2010/099313, Sep. 2, 2010.

International Patent Application No. PCT/US2013/042745 entitled "Insulin-Pramlintide Compositions and Methods for Making and Using Them", filed May 24, 2013; International Application Publication No. WO 2013/177565, Nov. 28, 2013.

U.S. patent application Ser. No. 13/637,359 entitled "Method, System, and Computer Program Product for Improving the Accuracy of Glucose Sensors Using Insulin Delivery Observation in Diabetes", filed Sep. 25, 2012; U.S. Patent Application Publication No. 2013/0079613, Mar. 28, 2013.

International Patent Application No. PCT/US2011/029793 entitled "Method, System, and Computer Program Product for Improving the Accuracy of Glucose Sensors Using Insulin Delivery Observation in Diabetes", filed Mar. 24, 2011; International Patent Application Publication No. WO 2011/119832, Sep. 29, 2011.

U.S. patent application Ser. No. 13/634,040 entitled "Method and System for the Safety, Analysis, and Supervision of Insulin Pump Action and Other Modes of Insulin Delivery in Diabetes", filed Sep. 11, 2012; U.S. Patent Application Publication No. 2013/0116649, May 9, 2013.

International Patent Application No. PCT/US2011/028163 entitled "Method and System for the Safety, Analysis, and Supervision of Insulin Pump Action and Other Modes of Insulin Delivery in Diabetes", filed Mar. 11, 2011; International Patent Application Publication No. WO 2011/112974, Sep. 15, 2011.

U.S. patent application Ser. No. 13/394,091 entitled "Tracking the Probability for Imminent Hypoglycemia in Diabetes from Self-Monitoring Blood Glucose (SMBG) Data", filed Mar. 2, 2012; U.S. Patent Application Publication No. 2012/0191361, Jul. 26, 2012.

International Patent Application No. PCT/US2010/047711 entitled "Tracking the Probability for Imminent Hypoglycemia in Diabetes from Self-Monitoring Blood Glucose (SMBG) Data", filed Sep. 2, 2010; International Patent Application Publication No. WO 2011/028925, Mar. 10, 2011.

U.S. patent application Ser. No. 13/393,647 entitled "System, Method and Computer Program Product for Adjustment of Insulin Delivery (AID) in Diabetes Using Nominal Open-Loop Profiles", filed Mar. 1, 2012; U.S. Patent Application Publication No. 2012/0245556, Sep. 27, 2012.

International Patent Application No. PCT/US2010/047386 entitled "System, Method and Computer Program Product for Adjustment of Insulin Delivery (AID) in Diabetes Using Nominal Open-Loop Profiles", filed Aug. 31, 2010; International Application Publication No. WO 2011/028731, Mar. 10, 2011.

U.S. patent application Ser. No. 13/380,839 entitled "System, Method, and Computer Simulation Environment for In Silico Trials in Pre-Diabetes and Type 2 Diabetes", filed Dec. 25, 2011; U.S. Patent Application Publication No. 2012/0130698, May 24, 2012.

International Patent Application No. PCT/US2010/040097 entitled "System, Method, and Computer Simulation Environment for In Silico Trials in Prediabetes and Type 2 Diabetes", filed Jun. 25, 2010; International Application Publication No. WO 2010/151834, Dec. 29, 2010.

U.S. patent application Ser. No. 13/322,943 entitled "System Coordinator and Modular Architecture for Open-Loop and Closed-Loop Control of Diabetes", filed Nov. 29, 2011; U.S. Patent Application Publication No. 2012/0078067, Mar. 29, 2012.

International Patent Application No. PCT/US2010/036629 entitled "System Coordinator and Modular Architecture for Open-Loop and Closed-Loop Control of Diabetes", filed May 28, 2010; International Patent Application Publication No. WO 2010/138848, Dec. 2, 2010.

U.S. patent application Ser. No. 13/131,467 entitled "Method, System, and Computer Program Product for Tracking of Blood Glucose Variability in Diabetes", filed May 26, 2011; U.S. Patent Application Publication No. 2011/0264378, Oct. 27, 2011.

International Patent Application No. PCT/US2009/065725 entitled "Method, System, and Computer Program Product for Tracking of Blood Glucose Variability in Diabetes", filed Nov. 24, 2009; International Patent Application Publication No. WO 2010/062898, Jun. 3, 2010.

U.S. patent application Ser. No. 12/975,580 entitled "Method, System, and Computer Program Product for the Evaluation of Glycemic Control in Diabetes from Self-Monitoring Data", filed Dec. 22, 2010; U.S. Patent Application Publication No. 2012/0004512, Jan. 5, 2012.

U.S. patent application Ser. No. 11/305,946 entitled "Method, System, and Computer Program Product for the Evaluation of Glycemic Control in Diabetes from Self-Monitoring Data", filed Dec. 19, 2005; U.S. Pat. No. 7,874,985, issued Jan. 25, 2011.

U.S. patent application Ser. No. 10/240,228 entitled "Method, System, and Computer Program Product for the Evaluation of Glycemic Control in Diabetes from Self-Monitoring Data", filed Sep. 26, 2002; U.S. Pat. No. 7,025,425, issued Apr. 11, 2006.

International Patent Application No. PCT/US2001/009884 entitled "Method, System, and Computer Program Product for the Evaluation of Glycemic Control in Diabetes", filed Mar. 29, 2001; International Application Publication No. WO 2001/72208, Oct. 4, 2001.

U.S. patent application Ser. No. 12/674,348 entitled "Method, Computer Program Product and System for Individual Assessment of Alcohol Sensitivity", filed Feb. 19, 2010; U.S. Patent Application Publication No. 2011/0264374, Oct. 27, 2011.

U.S. patent application Ser. No. 12/665,149 entitled "Method, System and Computer Program Product for Evaluation of Insulin Sensitivity, Insulin/Carbohydrate Ratio, and Insulin Correction Factors in Diabetes from Self-Monitoring Data", filed Dec. 17, 2009; U.S. Patent Application Publication No. 2010/0198520, Aug. 5, 2010.

International Patent Application No. PCT/US2008/069416 entitled "Method, System and Computer Program Product for Evaluation of Insulin Sensitivity, Insulin/Carbohydrate Ratio, and Insulin Correction Factors in Diabetes from Self-Monitoring Data", filed Jul. 8, 2008; International Patent Application Publication No. WO 2009/009528, Jan. 15, 2009.

U.S. patent application Ser. No. 12/664,444 entitled "Method, System and Computer Simulation Environment for Testing of Monitoring and Control Strategies in Diabetes", filed Dec. 14, 2009; U.S. Patent Application Publication No. 2010/0179768, Jul. 15, 2010.

International Patent Application No. PCT/US2008/067725 entitled "Method, System and Computer Simulation Environment for Testing of Monitoring and Control Strategies in Diabetes", filed Jun. 20, 2008; International Patent Application Publication No. WO 2008/157781, Dec. 24, 2008.

U.S. patent application Ser. No. 12/516,044 entitled "Method, System, and Computer Program Product for the Detection of Physical Activity by Changes in Heart Rate, Assessment of Fast Changing Metabolic States, and Applications of Closed and Open Control Loop in Diabetes", filed May 22, 2009; U.S. Pat. No. 8,585,593, issued Nov. 19, 2013.

International Patent Application No. PCT/US2007/085588 entitled "Method, System, and Computer Program Product for the Detection of Physical Activity by Changes in Heart Rate, Assessment of Fast Changing Metabolic States, and Applications of Closed and Open Control Loop in Diabetes", filed Nov. 27, 2007; International Patent Application Publication No. WO2008/067284, Jun. 5, 2008.

U.S. patent application Ser. No. 12/159,891 entitled "Method, System and Computer Program Product for Evaluation of Blood Glucose Variability in Diabetes from Self-Monitoring Data", filed Jul. 2, 2008; U.S. Patent Application Publication 2009/0171589, Jul. 2, 2009.

International Patent Application No. PCT/US2007/000370 entitled "Method, System and Computer Program Product for Evaluation of Blood Glucose Variability in Diabetes from Self-Monitoring Data", filed Jan. 5, 2007; International Application Publication No. WO 2007/081853, Jul. 19, 2007.

U.S. patent application Ser. No. 12/065,257 entitled "Accuracy of Continuous Glucose Sensors", filed Feb. 28, 2008; U.S. Patent Application Publication No. 2008/0314395, Dec. 25, 2008.

International Patent Application No. PCT/US2006/033724 entitled "Method for Improvising Accuracy of Continuous Glucose Sensors and a Continuous Glucose Sensor Using the Same", filed Aug. 29, 2006; International Application Publication No. WO 2007027691, Mar. 8, 2007.

U.S. patent application Ser. No. 11/943,226 entitled "Systems, Methods and Computer Program Codes for Recognition of Patterns of Hyperglycemia and Hypoglycemia, Increased Glucose Variability, and Ineffective Self-Monitoring in Diabetes", filed Nov. 20, 2007; U.S. Patent Application Publication No. 2008/0154513, Jun. 26, 2008.

U.S. patent application Ser. No. 11/578,831 entitled "Method, System and Computer Program Product for Evaluating the Accuracy of Blood Glucose Monitoring Sensors/Devices", filed Oct. 18, 2006; U.S. Pat. No. 7,815,569, issued Oct. 19, 2010.

International Patent Application No. US2005/013792 entitled "Method, System and Computer Program Product for Evaluating the Accuracy of Blood Glucose Monitoring Sensors/Devices", filed Apr. 21, 2005; International Application Publication No. WO 2005/106017, Nov. 10, 2005.

U.S. patent application Ser. No. 10/524,094 entitled "Method, System, And Computer Program Product For The Processing Of Self-Monitoring Blood Glucose (SMBG) Data To Enhance Diabetic Self-Management", filed Feb. 9, 2005; U.S. Pat. No. 8,538,703, issued Sep. 17, 2013

International Patent Application No. PCT/US2003/025053 entitled "Managing and Processing Self-Monitoring Blood Glucose", filed Aug. 8, 2003; International Application Publication No. WO 2001/72208, Oct. 4, 2001.

International Patent Application No. PCT/US2002/005676 entitled "Method and Apparatus for the Early Diagnosis of Subacute, Potentially Catastrophic Illness", filed Feb. 27, 2002; International Application Publication No. WO 2002/67776, Sep. 6, 2002.

U.S. patent application Ser. No. 10/069,674 entitled "Method and Apparatus for Predicting the Risk of Hypoglycemia", filed Feb. 22, 2002; U.S. Pat. No. 6,923,763, issued Aug. 2, 2005.

International Patent Application No. PCT/US00/22886 entitled "METHOD AND APPARATUS FOR PREDICTING THE RISK OF HYPOGLYCEMIA", filed Aug. 21, 2000; International Application Publication No. WO 2001/13786, Mar. 1, 2001.

SUMMARY

Contained herein is a disclosure of method of treating diabetes. The method includes measuring interstitial fluid glucose concentration using a glucose monitor, receiving insulin delivery data to reconstruct historical insulin concentration of a patient, determining patient insulin sensitivity based on the measured interstitial fluid glucose concentration, the insulin delivery data, an estimated glucose rate of appearance, and an estimated insulin concentration, and determining a diabetes treatment regime specific to the patient at a specific time based on the determined patient insulin sensitivity. The measured interstitial fluid glucose concentration may be an approximation of patient blood glucose. The method may also include determining the estimated glucose rate of appearance from a meal compartment including a first meal absorption model and a second meal absorption model, where the first meal absorption model is faster than the second meal absorption model, and determining the estimated insulin concentration from an insulin compartment. The diabetes treatment regime of the method may include dispensing an insulin dose from an insulin delivery device to the patient. The insulin dose may be displayed so that an insulin dose may be dispensed using a syringe, an insulin pump, or an insulin pen.

Also disclosed is a method for determining an insulin dose including receiving interstitial fluid glucose concentration measurements of a glucose monitor, receiving insulin delivery data to reconstruct historical insulin concentration of a patient, determining patient insulin sensitivity based on the received interstitial fluid glucose concentration measurements, the received insulin dispensing data, an estimated glucose rate of appearance, and an estimated insulin concentration, and determining an insulin dose based on the determined patient insulin sensitivity that is specific to the patient. The received interstitial fluid glucose concentration may be an approximation of patient blood glucose. The method may also include determining the estimated glucose rate of appearance from a meal compartment including a first meal absorption model and a second meal absorption model, where the first meal absorption model is faster than the second meal absorption model, and determining the estimated insulin concentration from an insulin compartment. The method may include dispensing the insulin dose from an insulin pump to the patient. The method may also include basing the determined patient insulin sensitivity on a weighted value of the measured interstitial fluid glucose concentration. The method may also include compensating the determined patient insulin sensitivity for calibration and measurement noise. The method may also include receiving patient physical activity information, where the determined patient insulin sensitivity is further based on the received patient physical activity information. The method may also include receiving patient circadian rhythm information, where the determined patient insulin sensitivity is based in part on the received patient circadian rhythm information. The determined patient insulin sensitivity may be based in part on a specified patient dietary habit. The insulin dose may be displayed so that an insulin dose may be dispensed using a syringe, an insulin pump, or an insulin pen.

Also disclosed is a controller for determining an insulin dose based on patient insulin sensitivity including a communications module configured to receive interstitial fluid glucose concentration of a glucose monitor, and receive insulin delivery data to reconstruct historical insulin concentration of a patient, a patient insulin sensitivity determination module configured to determine patient insulin sensitivity based on the interstitial fluid glucose concentration, the insulin delivery data, an estimated glucose rate of appearance, and an estimated insulin concentration, and an insulin dosage calculation module configured to calculate an insulin dose based on the determined patient insulin sensitivity that is specific to a patient. The glucose monitor may be configured to provide the measured interstitial fluid glucose concentration as an approximation of patient blood glucose. An estimation module may be configured to calculate the estimated glucose rate of appearance based on a meal compartment including a first meal absorption model and a second meal absorption model, where the first meal absorption model is faster than the second meal absorption model, and the estimated insulin concentration is calculated from an insulin component. The patient insulin sensitivity determination module may be configured to receive a weighted value of the measured interstitial fluid glucose concentration. The patient insulin sensitivity determination module may compensate for calibration and measurement noise. The controller may include a patient physical activity module configured to collect patient physical activity information, where a patient insulin sensitivity determined by the patient insulin sensitivity determination module will be based in part on patient physical activity information collected by the patient physical activity module. The apparatus may include a patient physical activity module configured to collect patient circadian rhythm information, where the patient insulin sensitivity determined by the patient insulin sensitivity determination module is based in part on the patient circadian rhythm information. The patient insulin sensitivity may be based in part on a specified patient dietary habit. An apparatus may include a single housing enclosing the controller, the glucose monitor, the patient insulin sensitivity determination module, and the insulin dosage calculation module. The controller may cause the insulin dose to be displayed so that an insulin dose may be dispensed using a syringe, an insulin pump, or an insulin pen.

Also disclosed is a non-transitory computer readable recording medium encoded with a program comprising instructions causing a controller to determine an insulin dose. The program causes the controller to receive interstitial fluid glucose concentration measurements of a glucose monitor, receive insulin delivery data to reconstruct historical insulin concentration of a patient, determine patient insulin sensitivity based on the received interstitial fluid glucose concentration measurements, the received insulin pump data, an estimated glucose rate of appearance, and an estimated insulin concentration, and determine an insulin dose based on the determined patient insulin sensitivity that is specific to a patient. The received interstitial fluid glucose concentration may be an approximation of patient blood glucose. The program may cause the controller to determine the estimated glucose rate of appearance from a meal compartment including a first meal absorption model and a second meal absorption model, where the first meal absorption model is faster than the second meal absorption model, and to determine the estimated insulin concentration from an insulin compartment. The program may cause the controller to base the determined patient insulin sensitivity on a weighted value of the measured interstitial fluid glucose concentration. The program may cause the controller to compensate the determined patient insulin sensitivity for calibration and measurement noise. The program may cause the controller to receive patient physical activity information, where the determined patient insulin sensitivity is further based on the received patient physical activity information. The program may cause the controller to receive patient circadian rhythm information, wherein the determined patient insulin sensitivity is further based on the received patient circadian rhythm information. The determined patient insulin sensitivity may be further based on a specified patient dietary habit. The insulin dose may be displayed so that an insulin dose may be dispensed using a syringe, an insulin pump, or an insulin pen.

DETAILED DESCRIPTION

Figure 1:
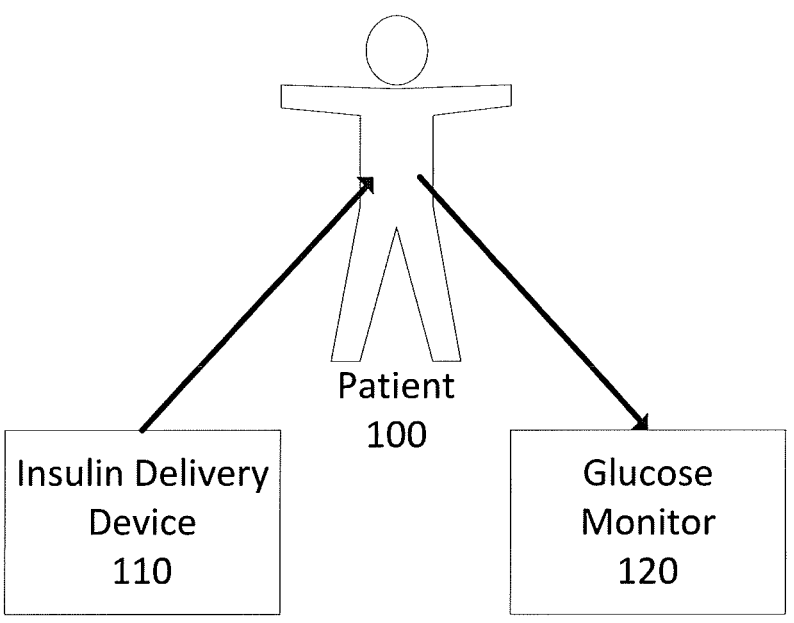
FIG. 1 depicts aspects utilized by the described techniques so that the patient may receive insulin.

To provide a more precise determination of the insulin sensitivity of a patient 100, the techniques described here should determine the value in a manner that allows for noise filtration for various inaccuracies. As described herein, the technique specified here recognizes that insulin sensitivity for a patient 100 is a dynamic and time-varying physiological parameter, and algorithms have been created that incorporate this recognition in a manner that improves the well-being of the patient 100.

One such algorithm is an adaptation of the Kalman filtering process which allows for state tracking by tunable noise filtration. Kalman filtering, also known as linear quadratic estimation, produces estimates of current state variables along with uncertainties. The next measurement is observed and the estimates are updated using a weighted average where higher weight is given to estimates with higher certainty.

In the technique described here, a first order insulin sensitivity dynamic was added to a nominal minimal model so that the insulin sensitivity state can be driven to an equilibrium value in a finite time period. More particularly, logarithmic transformations of blood glucose state, remote insulin action, and insulin sensitivity are applied. When the glucose-insulin model is embedded in a Kalman filter, the result is the following equation:

$$
\begin{bmatrix} \ln\left(\dfrac{G(k+1)}{G_b}\right) \\[2ex] \ln\left(\dfrac{X(k+1)}{X_b}\right) \\[2ex] \ln\left(\dfrac{SI(k+1)}{SI_b}\right) \end{bmatrix} = \tag{1}
$$

$$
\begin{bmatrix} -p_1 & -p_2 & -p_3 \\ 0 & -p_4 & 0 \\ 0 & 0 & -1/\tau_{SI} \end{bmatrix} \begin{bmatrix} \ln\left(\dfrac{G(k)}{G_b}\right) \\[2ex] \ln\left(\dfrac{X(k)}{X_b}\right) \\[2ex] \ln\left(\dfrac{SI(k)}{SI_b}\right) \end{bmatrix} + \begin{bmatrix} p_6 & 0 \\ 0 & p_4 \\ 0 & 0 \end{bmatrix} \begin{bmatrix} R_a(k) \\ I(k) \end{bmatrix}
$$

$R_a(k)$ and I(k) represent glucose rate of appearance and plasma insulin concentration respectively. These values, plus the measurement are input into the Kalman filter.

Without direct access, $R_a(k)$ and I(k) are computed by meal and insulin transport compartments separately.

The meal compartment includes at least two compartments. The first model $Q_1$ and the second model $Q_2$ represent meal absorption, where the first model represents a fast meal absorption model and the second model represents a slow meal absorption model. In at least some embodiments, the blood glucose appearance $R_a(k)$ is the sum of these two compartments.

The mathematical model for the meal compartment is reproduced below:

$$
\begin{bmatrix} Q_1(k+1) \\ Q_2(k+1) \end{bmatrix} = \begin{bmatrix} -(a_1+a_d) & 0 \\ a_d & -a_2 \end{bmatrix} \begin{bmatrix} Q_1(k) \\ Q_2(k) \end{bmatrix} + \begin{bmatrix} 1 \\ 0 \end{bmatrix} M(k) \tag{2}
$$

$$
R_a(k) = a_1 \cdot Q_1(k) + a_2 \cdot Q_2(k) \tag{3}
$$

The insulin model is reproduced below. VI is the insulin volume of distribution.

$$
\begin{bmatrix} I_{sc1}(k+1) \\ I_{sc2}(k+1) \\ I_p(k+1) \end{bmatrix} = \begin{bmatrix} -k_d & 0 & 0 \\ k_d & -k_d & 0 \\ 0 & k_d & -k_{cl} \end{bmatrix} \begin{bmatrix} I_{sc1}(k) \\ I_{sc2}(k) \\ I_p(k) \end{bmatrix} + \begin{bmatrix} 1 \\ 0 \\ 0 \end{bmatrix} J(k) \tag{4}
$$

$$
I(k) = \frac{I_p(k)}{VI \cdot BW} - I_b \tag{5}
$$

The resulting algorithm is a feed forward algorithm that determines the insulin sensitivity for the patient. Although the above description provides one embodiment of the algorithm used to determine the insulin sensitivity of the patient, other filters, algorithms, or techniques may be used as part of or to replace part of the described process. For example, frequency-weighed Kalman filters, extended Kalman filters, and unscented Kalman filters may be used as part of or to replace part of the described process so that the insulin patient determined for the patient may be more accurate.

In an exemplary embodiment, the above algorithm is embedded in a Kalman filter and is discretized as a five minute discrete system to match the interval at which a glucose monitor provides new data. The result of this model is as follows:

$$
\begin{bmatrix} \ln\left(\dfrac{G(k+1)}{G_b}\right) \\[2ex] \ln\left(\dfrac{X(k+1)}{X_b}\right) \\[2ex] \ln\left(\dfrac{SI(k+1)}{SI_b}\right) \end{bmatrix} = \begin{bmatrix} -p_1 & -p_2 & -p_3 \\ 0 & -p_4 & 0 \\ 0 & 0 & -\dfrac{1}{\tau_{SI}} \end{bmatrix} \tag{6}
$$

$$
\begin{bmatrix} \ln\left(\dfrac{G(k)}{G_b}\right) \\[2ex] \ln\left(\dfrac{X(k)}{X_b}\right) \\[2ex] \ln\left(\dfrac{SI(k)}{SI_b}\right) \end{bmatrix} + \begin{bmatrix} p_6 & 0 \\ 0 & \dfrac{p_4}{VI \cdot BW} \\ 0 & 0 \end{bmatrix} \begin{bmatrix} R_a(k) \\ I_p(k) \end{bmatrix} + Gw[k]
$$

-continued $$\left[\ln\left(\frac{G(k)}{G_b}\right)\right] = \begin{bmatrix}1 & 0 & 0\end{bmatrix}\begin{bmatrix}\ln\left(\frac{G(k)}{G_b}\right)\\ \ln\left(\frac{X(k)}{X_b}\right)\\ \ln\left(\frac{SI(k)}{SI_b}\right)\end{bmatrix} + Du[n] + Hw[n] + v[k] \qquad 7)$$

The values w[n] and v[n] in this embodiment represent processing noise and measurement noise respectively. The tuning factors are defined as noise covariance as $E(w[n]w[n]^T)=Q$, $E(v[n]v[n]^T)=R$, $E(w[n]v[n]^T)=N$. The gain L is found by solving the discrete Riccati equation and is equal to $(APC^T+\overline{N})(CPC^T+\overline{R})^{-1}$, where $\overline{R}=R+HN+N^TH^T+HQH^T$ and $\overline{N}=G(QH^T+N)$. In an exemplary embodiment, the state estimate is adjusted based on the priori estimate $\hat{x}^-[n]$ by adding a weighted sensor measurement, y as shown below:

$$\hat{x}[n]=\hat{x}^-[n]+L(y[n]-C\cdot\hat{x}^-[n]) \qquad 8)$$

Examples of the matrices and covariances are listed in the below table that may be obtained are identified below:

| G | H | Q | R | N |
|---|---|---|---|---|
| $\begin{bmatrix}0.05 & 0 & 0\\ 0 & 0 & 0\\ 0 & 0 & 1\end{bmatrix}$ | $\begin{bmatrix}0 & 0 & 0\end{bmatrix}$ | $\begin{bmatrix}1 & 0 & 0\\ 0 & 1 & 0\\ 0 & 0 & 1\end{bmatrix}$ | 0.5 | $\begin{bmatrix}0 & 0 & 0\end{bmatrix}'$ |

The matrices and covariances were derived from an exemplary embodiment which assumed that the analogous insulin action ln $$\left(\frac{X}{X_b}\right)$$

has no process noise. The assignment of process noise for ln $$\left(\frac{G}{G_b}\right)$$

and ln $$\left(\frac{SI}{SI_b}\right)$$

was decided by considering two aspects: units and physiological magnitudes. Although these were the assumptions employed to derive the above matrices and covariances, the algorithm itself is not, however, limited to these described assumptions.

The methods and systems that apply these algorithms will now be discussed. As shown in FIG. 1, these techniques involve a patient 100, an insulin delivery device 110 for delivering insulin to the patient, and a glucose monitor 120 for monitoring the patient glucose levels. In addition to insulin, the insulin delivery device 110 also provides insulin delivery data that may be read. In some embodiments, the insulin delivery device 110 may include components such as a wireless radio so that communication with an external device such as a smartphone, personal computer, or other suitable device is possible. In other embodiments, the insulin delivery device 110 may be a syringe or an insulin pen that provides a specific dose of insulin, but requires human interaction to trigger the injection of insulin. The glucose monitor 120 measures interstitial fluid glucose concentration using known techniques. Some embodiments of the glucose monitor 120 include a glucose sensor that is inserted underneath the skin of the patient 100 so that glucose levels in tissue fluid may be measured. Embodiments of the glucose monitor 120 may include components such as a wireless radio so that communication with an external device such as a smartphone, personal computer, or other suitable device is possible. The glucose monitor 120 may provide measurements of the interstitial fluid glucose concentration at particular intervals such as once every minute, once every five minutes, and the like. The information from the insulin delivery device 110 and the glucose monitor 120 are used in an algorithm that determines the insulin sensitivity of the patient 100 where the algorithm recognizes insulin sensitivity is a time-varying physiological parameter. The glucose monitor 120 may include components such as a wireless radio so that communication with an external device such as a smartphone, personal computer, or other suitable device is possible.

Figure 2:
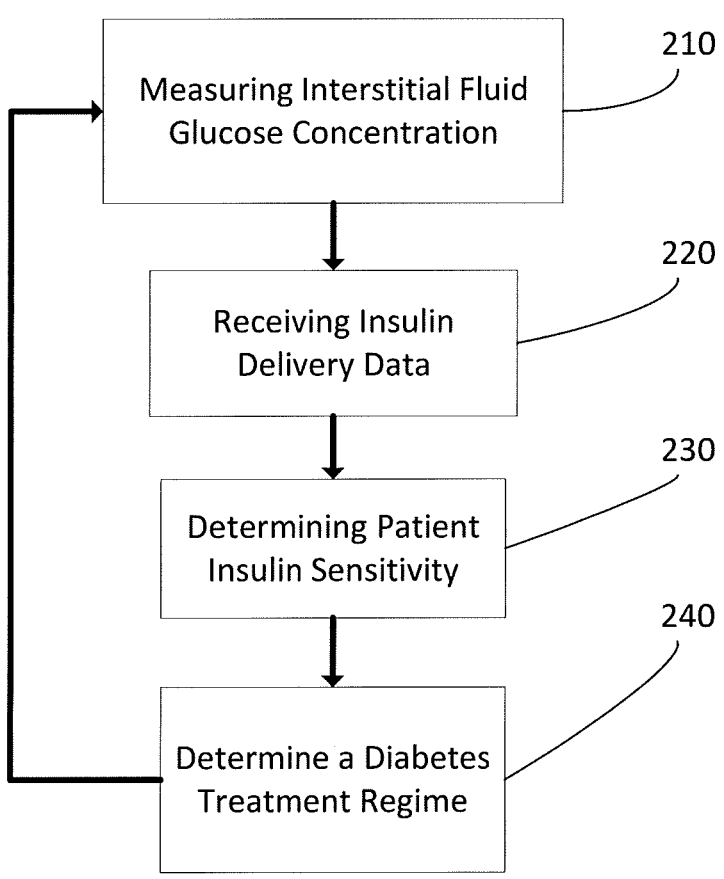
FIG. 2 depicts the process for treating diabetes.

The recognition of the time-varying nature of the insulin sensitivity of a patient allows for a more tailored and patient specific approach to diabetes treatment that considers the changes in a patient's physiology over time and makes any needed adjustments to the patient's treatment plan. FIG. 2 depicts a process 200 for treating diabetes by determining an insulin dose based on patient insulin sensitivity. The treatment process 200 includes a step 210 of measuring interstitial fluid glucose concentration using a glucose monitor 120. The interstitial fluid glucose concentration may be an approximation of patient blood glucose. In some embodiments, the patient blood glucose is directly measured instead of the interstitial fluid glucose concentration. As discussed above, the glucose monitor 120 provides measurements using known techniques and may provide these measurements at periodic intervals.

The treatment process 200 also includes a step 220 of receiving insulin delivery data to reconstruct historical insulin concentration of a patient. The historical insulin concentration of the patient is based on the amount of insulin that has already been delivered to the patient. The time period encompassed by the historical insulin concentration depends on the treatment regimes prescribed to the patient. For example, if a historical trend of decreasing insulin sensitivity is to be confirmed, the treatment process 200 will receive insulin delivery data at step 220 that considers an appropriately sized set of insulin concentrations so that such trends can be discerned. In other instances, if the patient has a circadian rhythm that is increasing the patient's insulin sensitivity, the treatment process 200 will receive insulin delivery data at step 220 that considers an appropriately sized set of insulin concentrations so that the patient's circadian rhythm and increasing insulin sensitivity is confirmed. The insulin delivery data may include information such as the number of pump cycles that have occurred in a given period of time, the number of milliliters that have been dispensed in a given period of time, or other types of information suitable for determining the historical insulin concentration of a patient. The insulin delivery data may also include the initial concentration of insulin that was delivered during the given period of time.

The step 230 involves determining the insulin sensitivity of the patient 100 based on the interstitial fluid glucose concentrated measured at step 210, the insulin delivery data read at step 220, an estimated glucose rate of appearance, and an estimated insulin concentration. In some embodiments, the estimated glucose rate of appearance is determined from a meal compartment with a first meal absorption model and a second meal absorption model. The first meal absorption model is faster than the second meal absorption model. The estimated insulin concentration is determined from an insulin compartment.

Once the patient insulin sensitivity is determined, step 240 involves determining a diabetes treatment regime specific to the patient at a specific time based on the determined patient insulin sensitivity. The determined treatment regime may include dietary changes, exercise, non-insulin based medications, or insulin delivered by a syringe, insulin pen, insulin pump, or the like. If insulin is not needed, the process returns to step 210 and restarts the process. In some embodiments, the treatment process 200 is performed at intervals that are based on the collection frequency of the glucose monitor 120. For example, the treatment process 200 may execute at five minute intervals when the glucose monitor 120 provides new measurements in five minute intervals.

Figure 3:
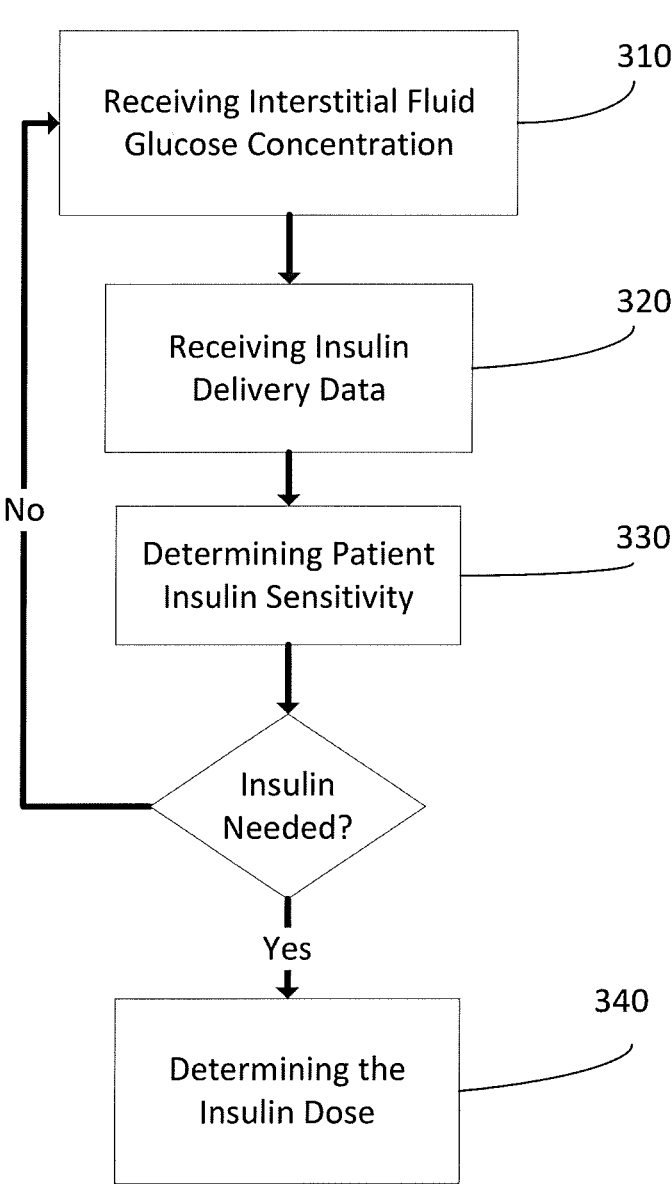
FIG. 3 depicts the method for dispensing insulin based on patient insulin sensitivity.

A method 300 of determining an insulin dose based on patient insulin sensitivity is depicted in FIG. 3. This method 300 includes the step 310 of receiving interstitial fluid glucose concentrations of a glucose monitor 120. As discussed above, the glucose monitor 120 provides measurements using known techniques and may provide these measurements at periodic intervals.

The method 300 also includes the step 320 of receiving insulin delivery data from the insulin pump 110 to determine the historical insulin concentration of a patient. The historical insulin concentration of the patient is based on the amount of insulin that has already been delivered to the patient. The time period encompassed by the historical insulin concentration depends on the treatment regimes available to the patient. For example, if a historical trend of decreasing insulin sensitivity is to be confirmed, the treatment process 200 will receive insulin delivery data at step 220 that considers an appropriately sized set of insulin concentrations so that such trends can be discerned. In other instances, if the patient has a circadian rhythm that is increasing the patient's insulin sensitivity, the treatment process 200 will receive insulin delivery data at step 220 that considers an appropriately sized set of insulin concentrations so that the patient's circadian rhythm and increasing insulin sensitivity is confirmed. The insulin pump data may include information such as the number of pump cycles that have occurred in a given period of time, the number of milliliters that have been dispensed in a given period of time, or other types of information suitable for determining the historical insulin concentration of a patient. The insulin delivery data may also include the initial concentration of insulin that was delivered during the given period of time.

Step 330 of the method 300 determines the insulin sensitivity of the patient 100 based on the received interstitial fluid glucose concentration measurements, the received pump data, an estimated glucose rate of appearance, and an estimated insulin concentration. An insulin dose is determined at step 340 based on the determined patient insulin sensitivity. In some embodiments, the interstitial fluid glucose concentration that is received is an approximation of patient blood glucose. Embodiments of the method 300 may include determining the estimated glucose rate of appearance from a meal compartment including a first meal absorption model and a second meal absorption model. The first meal absorption model is faster than the second meal absorption model. The estimated insulin concentration is determined from an insulin compartment.

Once insulin sensitivity of the patient 100 is determined, a decision is made as to the treatment regime for the patient 100. In this method 300, the treatment regime includes whether insulin is needed for the patient 100, and the appropriate dosage to deliver to the patient based on the determined patient insulin sensitivity. If insulin is needed, step 340 determines the insulin dose based on the determined patient sensitivity specific to the patient. The determined insulin dose may be delivered using a syringe, an insulin pump, an insulin pen, or the like. If insulin is not needed, the method 300 returns to step 310 and restarts the method 300. In some embodiments, the method 300 is performed at intervals that are based on the collection frequency of the glucose monitor 120. For example, the method 300 may execute at five minute intervals when the glucose monitor 120 provides new measurements in five minute intervals. The method 300 may be performed at any desired interval so that the patient 100 receives the needed insulin dosage.

Embodiments of the method 300 may also determine patient insulin sensitivity on a weighted value of the measured interstitial fluid glucose concentration. In some embodiments of the method 300, the determined patient insulin sensitivity compensates for calibration and measurement noise. In other embodiments of the method 300, physical activity information is received, and the patient insulin sensitivity is based on the received patient physical activity information. Such physical activity information may include the number of calories expended, the duration of physical activity, the intensity of physical activity, and other information useful for helping determine patient insulin sensitivity information. In some embodiments of the method 300, the circadian rhythm information of the patient 100 is received and the determined patient insulin sensitivity is based in part on the received patient circadian rhythm information. Certain embodiments of the method 300 also consider specified patient dietary habits when determining patient insulin sensitivity.

Figure 4:
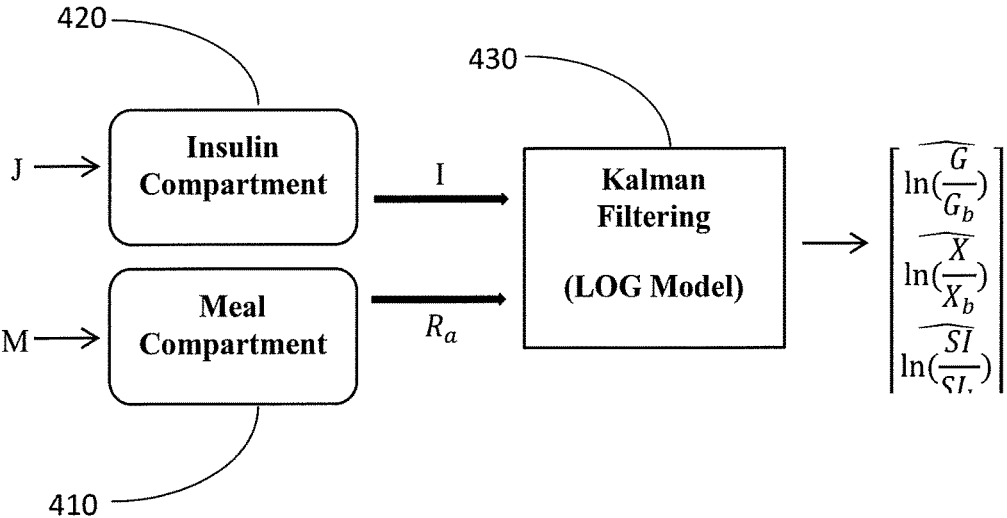
FIG. 4 depicts the schematic diagram of the feed-forward structure of the process.

FIG. 4 depicts the meal compartment 410 and the insulin compartment 420. The meal compartment 410 has two compartments, where one compartment $Q_1$ may represent fast meal absorption, and where another compartment $Q_2$ may represent slow meal absorption. The meal compartment 410 may be mathematically represented as follows:

$$\begin{bmatrix} Q_1(k+1) \\ Q_2(k+1) \end{bmatrix} = \begin{bmatrix} -(a_1+a_d) & 0 \\ a_d & -a_2 \end{bmatrix}\begin{bmatrix} Q_1(k) \\ Q_2(k) \end{bmatrix} + \begin{bmatrix} 1 \\ 0 \end{bmatrix}M(k) \qquad 9)$$

$$R_a(k) = a_1 \cdot Q_1(k) + a_2 \cdot Q_2(k) \qquad 10)$$

The insulin compartment 420 determines the insulin volume of distribution (VI) and is mathematically represented as follows:

$$\begin{bmatrix} I_{sc1}(k+1) \\ I_{sc2}(k+1) \\ I_p(k+1) \end{bmatrix} = \begin{bmatrix} -k_d & 0 & 0 \\ k_d & -k_d & 0 \\ 0 & k_d & -k_{cl} \end{bmatrix}\begin{bmatrix} I_{sc1}(k) \\ I_{sc2}(k) \\ I_p(k) \end{bmatrix} + \begin{bmatrix} 1 \\ 0 \\ 0 \end{bmatrix}J(k) \qquad 11)$$

$$I(k) = \frac{I_p(k)}{VI \cdot BW} - I_b \qquad 12)$$

The glucose rate of appearance $R_a$ and the plasma insulin concentration $I(k)$ are therefore calculated without requiring directly measured values for glucose rate of appearance and plasma insulin concentration. These calculated values are passed to the Kalman filter 430 for determination of the insulin sensitivity of the patient 100. This provides a feed-forward model that is based on a mathematical model of the behavior of the glucose rate of appearance and the plasma insulin concentration in a patient 100.

A controller 500 for determining an insulin dose based on patient insulin sensitivity will now be described. The controller 500 shown in FIG. 5 includes a communications module configured to receive interstitial fluid glucose concentration of a glucose monitor 520, and receive insulin delivery data to determine the insulin concentration of a patient. The controller 500 also includes a patient insulin sensitivity determination module 540 that is configured to determine the insulin sensitivity of the patient 100. The insulin sensitivity is based on measured interstitial fluid glucose concentration from the glucose monitor 120, the concentration of insulin of the patient, estimated glucose rate of appearance, and estimated insulin concentration. An insulin dosage calculation module 550 is configured to calculate an insulin dose based on the determined patient insulin that is specific to a patient.

In one embodiment where the insulin delivery device is an insulin pump 510, an insulin pump controller receives an insulin dosage and the insulin pump 510 is operated so that the dose for the calculated insulin sensitivity of the patient 100 is provided. In addition to receiving the dosage commands, the insulin pump controller may control other aspects of the insulin pump 510. In at least some embodiments, an apparatus that includes a housing enclosing the controller 500, insulin pump 510, the glucose monitor 520, the module 530, the patient insulin sensitivity determination module 540, and the insulin dosage calculation module 550. In this embodiment where the controller 500 is part of an apparatus, each component is electrically connected to each other within the housing that forms a small device suitable for placement on the body of the patient 100. Other necessary components such as a power source, memory for storing instructions and data, and other components necessary to implement the techniques described here in a controller configured to perform the described functions in an apparatus for usage by the patient 100 are contemplated but not explicitly described here.

Figure 5:
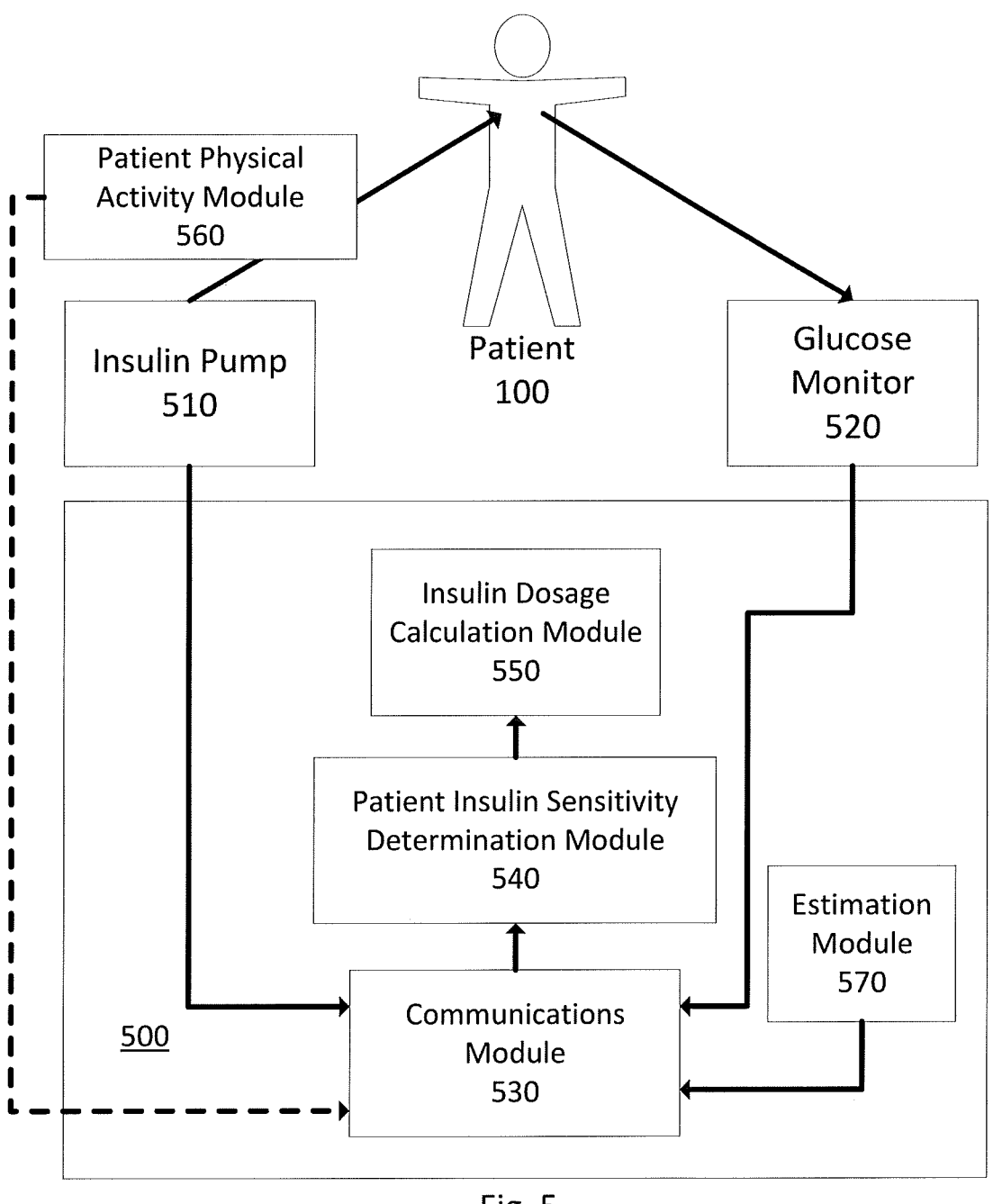
FIG. 5 depicts a controller for determining an insulin dose.

In some embodiments, certain components such as the insulin pump 510 or the glucose monitor 520 may be separate from the apparatus so that these aspects may be placed on the patient 100 in a more comfortable manner. For example, the glucose monitor 520 may be placed under the skin of the patient 100 and the insulin pump 510 may be placed in another discrete location on the body of the patient 100. As depicted in FIG. 5, the patient physical activity module 560, described later, is an external component that communicates with the apparatus 500. In such an embodiment, components of the apparatus such as the patient physical activity module 560 may communicate with each other using wired or wireless communications systems. In a wireless embodiment, the components placed external to the main apparatus 500 may communicate using Bluetooth™, Wi-Fi™, ZigBee™, or another appropriate communications protocol. In such an embodiment, the apparatus and the external devices will include the appropriate modules for communications. In certain embodiments, the apparatus including external components may communicate with the patient or a medical professional using the wired or wireless communications system. Such communications could include the retrieval of historically measured interstitial fluid glucose concentrations, historical volume of insulin distribution data, historical predictions of the time-varying physiological parameter, historical patient insulin sensitivity determinations, and historical instructions transmitted to the insulin pump controller. Such information may be retained for medical purposes and for apparatus diagnostic purposes, for example. Such information may also be accessible by the patient 100 so that he or she can also monitor his or her medical condition and also monitor the operation of the apparatus.

In at least some embodiments, the various modules of the controller 500 may be incorporated into a single physical controller 500 that implements the functions of modules such as the communications module 530, the patient insulin sensitivity determination module 540, and/or the insulin dosage calculation module 550. Such integration of components helps minimize costs and reduce power consumption. In another embodiment, the controller 500 may incorporate other functions such as aspects of the insulin pump 510, the insulin pump controller, and the glucose monitor 520 for example. Such a controller 500 may handle any data processing needed to operate the insulin pump 510, to control the insulin pump 510 to dispense the desired amount of insulin, and to monitor the glucose levels of the patient 100. Such a controller 500 may also manage other aspects of the apparatus including the power consumption of the apparatus, the storage of historical information, and other functions needed for the operation of the apparatus. In certain embodiments, multiple controllers 500 may be employed so that each controller 500 may be specifically configured to execute the assigned functions in an efficient manner.

The apparatus may include a housing enclosing the controller 500 along with a glucose monitor 520 that is configured to provide the measured interstitial fluid glucose concentrations as an approximation of patient blood glucose. In embodiments that can obtain measurements of patient blood glucose, this value may be measured in addition to, or in lieu of, the interstitial fluid glucose concentration. An estimation module 570 may be configured to determine the estimated glucose rate of appearance based on a meal compartment including a first meal absorption model and a second meal absorption model, where the first meal absorption model is faster than the second meal absorption model, and configured to determine the estimated insulin concentration which is determined from an insulin compartment. The patient insulin sensitivity determination module 540 may be configured to receive a weighted value of the measured interstitial fluid glucose concentration. In some embodiments, the patient insulin sensitivity determination module 540 may be configured to compensate for calibration and measurement noise.

Some embodiments of the apparatus may include components for presenting a user interface such as a display and input devices such as a touchscreen, a physical button, a switch, or the like. By including components for a user interface, the patient 100 may quickly assess their current insulin status and administering an insulin dose using a variety of delivery methods such as a syringe, an insulin pen, or an insulin pump 510, for example.

As discussed above, the techniques for determining insulin sensitivity described here recognize that patient insulin sensitivity varies depending on a variety of factors, and also varies over time. Accordingly, to improve the determination of the insulin sensitivity of the patient 100 some embodiments of the apparatus include a patient physical activity module 560 so that physical activity information of the patient 100 may be collected. In some embodiments, the patient physical activity module 560 collects circadian rhythm information from the patient 100. Certain embodiments of the apparatus may include a patient physical activity module 560 which collect both types of information with the patient physical activity module 560, or additional information. Exemplary embodiments of the patient physical activity module 560 may include sensors such as accelerometers, barometers, global positioning system (GPS) receivers, and other sensors useful for monitoring the physical activity of the patient 100. Embodiments of the patient physical activity module 560 may be configured to transmit the physical activity information as information is being collected, or configured to accumulate the physical activity information until transmission to the apparatus for consideration by the patient insulin sensitivity determination module 540 is possible.

In at least some embodiments, the patient physical activity module 560 is an external component that communicates with the apparatus. Such an embodiment allows for the patient physical activity module 560 to be placed on the patient 100 at a location that does not interfere with the physical activity of the patient 100. In some embodiments, the patient physical activity module 560 may be enclosed in the housing with other aspects of the apparatus. In one embodiment, conventional activity trackers may interface with the apparatus so that information already being collected by the patient 100 using the conventional activity tracker may be considered by the apparatus when determining patient insulin sensitivity. In such an embodiment, a controller may need to process the information being received from the conventional activity tracker so that patient insulin sensitivity may be easily derived.

In some embodiments, the physical activity module 560 processes the information received from the sensors before transmitting the information for consideration by the patient insulin sensitivity determination module 540. For example, the physical activity module 560 may process the sensor information in a manner that provides a uniform data format for consideration by the patient insulin sensitivity determination module 540. In such an embodiment, the patient insulin sensitivity determination module 540 need not process the underlying sensor information and can instead offload this processing to the patient physical activity module 560. In another embodiment, the patient insulin sensitivity determination module 540 has access to the underlying sensor information to improve the determination of the insulin sensitivity of the patient 100. Embodiments of the apparatus may also consider a specified patient dietary habit when determining the patient insulin sensitivity. Such dietary habit information may be input using a computing device or a dedicated input device in communication with the apparatus.

Figure 6:
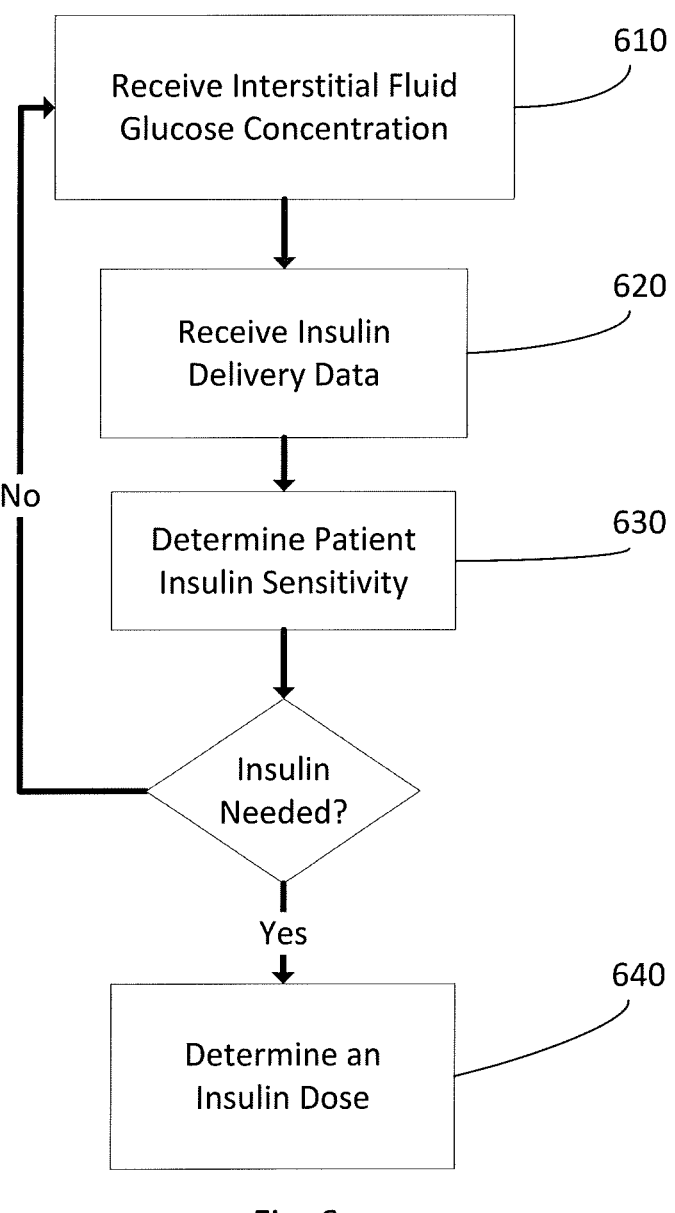
FIG. 6 depicts the process for determining an insulin dose executed by a controller that receives instructions encoded in a program.

FIG. 6 depicts the process 600 executed by a controller that receives the instructions from a program written to perform the process 600 for determining an insulin dose based on patient insulin sensitivity. As described above, the controller may be a single controller configured to execute the functions of the modules of an apparatus. For example, such a controller may incorporate the functionality of the prediction module 530 and the patient insulin sensitivity determination module 540 into a single physical controller to help minimize costs and reduce power consumption. The controller may also perform other functions necessary for the operation of a device performing the process 600. For example, the controller may perform power management functions or communications functions to ensure the continual and reliable performance of the process 600. In an apparatus implementing the process 600 described here, the controller may access the program from non-transitory computer readable media such as a hard drive, solid state memory, optical storage, or other storage media. In some embodiments, the process 600 may be implemented on an integrated circuit such as a field-programmable gate array with an array of programmable logic blocks and a hierarchy of reconfigurable interconnects allowing the programmable logic blocks to be wired together to perform the desired functions.

The process 600 of dispensing insulin based on patient insulin sensitivity includes the step 610 of receiving interstitial fluid glucose concentrations of a glucose monitor 120, 520. The process 600 also includes the step 620 of receiving insulin delivery data to determine the historical insulin concentration of the patient. The historical insulin concentration of the patient is based on the amount of insulin that has already been delivered to the patient. The time period encompassed by the historical insulin concentration depends on the treatment regimes available to the patient. For example, if a historical trend of decreasing insulin sensitivity is to be confirmed, the treatment process 200 will receive insulin delivery data at step 220 that considers an appropriately sized set of insulin concentrations so that such trends can be discerned. In other instances, if the patient has a circadian rhythm that is increasing the patient's insulin sensitivity, the treatment process 200 will receive insulin delivery data at step 220 that considers an appropriately sized set of insulin concentrations so that the patient's circadian rhythm and increasing insulin sensitivity is confirmed. The insulin delivery data may include information such as the number of pump cycles that have occurred in a given period of time, the number of milliliters that have been dispensed in a given period of time, or other types of information suitable for determining the historical insulin concentration of a patient. The insulin delivery data may also include the initial concentration of insulin that was delivered during the given period of time.

Step 630 of the process 600 determines the insulin sensitivity of the patient 100 based on the received interstitial fluid glucose concentration measurements, the received pump data, an estimated glucose rate of appearance, and an estimated insulin concentration. As discussed above, the glucose monitor 120 provides measurements using known techniques and may provide these measurements at periodic intervals.

Once the patient insulin sensitivity is determined, a decision is made as to the treatment regime for the patient 100. In this process 600, the treatment regime includes whether insulin is needed for the patient 100, and the appropriate dosage to deliver to the patient based on the determined patient insulin sensitivity. If insulin is needed, step 640 involves controlling the insulin pump 110, 510 to dispense an insulin dose based on the determined patient sensitivity. The determined insulin dose may be delivered using a syringe, an insulin pump, an insulin pen, or the like. If insulin is not needed, the process 600 returns to step 610 and restarts the process 600. In some embodiments, the process 600 is performed at intervals that are based on the collection frequency of the glucose monitor 120, 520. For example, the process 600 may execute at five minute intervals when the glucose monitor 120, 520 provides new measurements in five minute intervals. The process 600 may be performed at any desired interval so that the patient 100 receives the needed insulin dosage.

An insulin pump 110, 510 may be controlled to dispense an insulin dose based on the insulin dose. In some embodiments, the interstitial fluid glucose concentration that is received is an approximation of patient blood glucose. Embodiments of the process 600 may include determining the estimated glucose rate of appearance from a meal compartment including a first meal absorption model and a second meal absorption model. The first meal absorption model is faster than the second meal absorption model. The estimated insulin concentration is determined from the insulin component.

Embodiments of the process 600 may also determine patient insulin sensitivity on a weighted value of the measured interstitial fluid glucose concentration. In some embodiments of the process 600, the determined patient insulin sensitivity compensates for calibration and measurement noise. In other embodiments of the process 600, physical activity information is periodically received where the patient insulin sensitivity is based on the received patient physical activity information. Such physical activity information may include the number of calories expended, the duration of physical activity, the intensity of physical activity, and other information useful for helping determine patient insulin sensitivity information. In some embodiments of the process 600, the circadian rhythm information of the patient 100 is received and the determined patient insulin sensitivity is based in part on the received patient circadian rhythm information. Certain embodiments of the process 600 also consider specified patient dietary habits when determining patient insulin sensitivity.

By performing the techniques disclosed here that contemplate the time-varying nature of insulin sensitivity in a patient, the patient 100 with diabetes enjoys a more effective treatment regimen because the diabetes treatment plan, which may include an appropriate insulin dosage, considers the dynamic insulin sensitivity of the patient. By employing a closed-loop control system, the insulin dosages given to the patient 100 will be informed by the insulin sensitivity of the patient 100 that is derived from these described techniques.

Techniques consistent with the present disclosure provide, among other features, systems and methods for identification of pre-approved products in a limited use account. While various exemplary embodiments of the disclosed system and method have been described above, it should be understood that they have been presented for purposes of example only, not limitations. It is not exhaustive and does not limit the disclosure to the precise form disclosed. Modifications and variations are possible in light of the above teachings or may be acquired from practicing of the disclosure, without departing from the breadth or scope.

What is claimed is:

1. A controller for an insulin dispensing device, the controller comprising:

a communications module configured to receive interstitial fluid glucose concentration from a glucose monitor, and receive insulin delivery data;

a patient insulin sensitivity determination module configured to determine patient insulin sensitivity based on the interstitial fluid glucose concentration, the insulin delivery data, an estimated glucose rate of appearance, and an estimated insulin concentration, wherein:

the patient insulin sensitivity determination module is configured to use the interstitial fluid glucose concentration as an approximation of patient blood glucose; and the patient insulin sensitivity determination module is configured to determine the estimated glucose rate of appearance using a meal compartment including a first meal absorption model compartment and a second meal absorption modelcompartment, the first meal absorption compartment being faster than the second meal absorption compartment, wherein the estimated glucose rate of appearance is determined from the meal compartment based on a summation of the first meal absorption compartment and the second meal absorption compartment; and an insulin dosage calculation module configured to modify an insulin dose by adjusting one or more of a rapid-acting insulin dosage amount, a short-acting insulin dosage amount, an intermediate-acting insulin dosage amount, a long-acting insulin dosage amount, or a pre-mixed insulin dosage amount based on the determined patient insulin sensitivity that is specific to a patient; and wherein the communication module causes the insulin dispensing device to dispense the modified insulin dose to the patient.

2. The controller of claim 1, comprising:

an estimation module configured to calculate the estimated glucose rate of appearance and the estimated insulin concentration, wherein the estimated insulin concentration is determined from an insulin compartment.

3. The controller of claim 1, wherein at least one of the estimated glucose rate of appearance or the estimated insulin concentration is estimated based on an adaptation of a Kalman filtering process.

4. The controller of claim 1, wherein the patient insulin sensitivity determination module is configured to receive a weighted value of the measured interstitial fluid glucose concentration.

5. The controller of claim 1, wherein the patient insulin sensitivity determination module is configured to compensate for calibration and measurement noise.

6. The controller of claim 1, comprising:

a patient physical activity module configured to collect patient physical activity information, wherein a patient insulin sensitivity determined by the patient insulin sensitivity determination module will be based in part on patient physical activity information collected by the patient physical activity module.

7. The controller of claim 1, comprising:

a patient physical activity module configured to collect patient circadian rhythm information;

wherein the patient insulin sensitivity determined by the patient insulin sensitivity determination module will based in part on the patient circadian rhythm information.

8. The controller of claim 1, wherein the patient insulin sensitivity is based in part on a specified patient dietary habit.

9. The controller of claim, 1 in combination with a single housing enclosing at least the glucose monitor, the patient insulin sensitivity determination module, and the insulin dosage calculation module.

10. The controller of claim 1, in combination with the display device, wherein the display device is configured to display information related to the calculated insulin dose.

11. A device for administering insulin, the device comprising:

a controller including at least one operating module, the controller configured to:

receive interstitial fluid glucose concentration measurements from a glucose monitor;

receive insulin delivery data;

determine patient insulin sensitivity based on the received interstitial fluid glucose concentration measurements, the received insulin delivery data, an estimated glucose rate of appearance, and an estimated insulin concentration, wherein:

the interstitial fluid glucose concentration is used as an approximation of patient blood glucose; and the estimated glucose rate of appearance is determined from a meal compartment including a first meal absorption compartment and a second meal absorption compartment, the first meal absorption compartment being faster than the second meal absorption compartment, wherein the estimated glucose rate of appearance is determined from the meal compartment based on a summation of the first meal absorption compartment and the second meal absorption compartment;

modify an insulin dose by adjusting one or more of a rapid-acting insulin dosage amount, a short-acting insulin dosage amount, an intermediate-acting insulin dosage amount, a long-acting insulin dosage amount, or a pre-mixed insulin dosage amount based on the determined patient insulin sensitivity that is specific to a patient; and dispense the modified insulin dose to the patient.

12. The device of claim 11, wherein the device is configured to determine the estimated insulin concentration from an insulin compartment.

13. The device of claim 11, wherein at least one of the estimated glucose rate of appearance or the estimated insulin concentration is estimated based on an adaptation of a Kalman filtering process.

14. The device of claim 11, wherein the determined patient insulin sensitivity is based on a weighted value of the measured interstitial fluid glucose concentration.

15. The device of claim 11, wherein the device is configured to compensate the determined patient insulin sensitivity for calibration and measurement noise.

16. The device of claim 11, wherein the device is configured to receive patient physical activity information, and wherein the determined patient insulin sensitivity is based on the received patient physical activity information.

17. The device of claim 11, wherein the device is configured to receive patient circadian rhythm information, and wherein the determined patient insulin sensitivity is based on the received patient circadian rhythm information.

18. The device of claim 11, wherein the determined patient insulin sensitivity is based on a specified patient dietary habit.

* * * * *